United States Patent
Bertz et al.

(10) Patent No.: US 7,166,275 B2
(45) Date of Patent: Jan. 23, 2007

(54) COMPOSITIONS CONTAINING PHENETHYL ARYL ESTERS AS SOLUBILIZING AGENTS FOR ACTIVE ORGANIC COMPOUNDS

(75) Inventors: Steven H. Bertz, Morristown, NJ (US); Samuel T. D'Arcangelis, Randolph, NJ (US); Ilya Makarovsky, Fair Lawn, NJ (US); Mark Rerek, Scotch Plains, NJ (US)

(73) Assignee: ISP Investments Inc., Wilmington, DE (US)

( * ) Notice: Subject to any disclaimer, the term of this patent is extended or adjusted under 35 U.S.C. 154(b) by 281 days.

(21) Appl. No.: 10/617,497

(22) Filed: Jul. 11, 2003

(65) Prior Publication Data

US 2005/0008586 A1     Jan. 13, 2005

(51) Int. Cl.
*A61K 7/42* (2006.01)
(52) U.S. Cl. .......................................... 424/59; 424/60
(58) Field of Classification Search ................. 424/59, 424/60
See application file for complete search history.

(56) References Cited

U.S. PATENT DOCUMENTS

| | | | |
|---|---|---|---|
| 4,791,097 A | | 12/1988 | Walele et al. |
| 5,833,999 A | * | 11/1998 | Trinh et al. ................. 424/401 |
| 5,998,120 A | | 12/1999 | Connelly et al. |
| 6,589,921 B2 | * | 7/2003 | Herrmann et al. .......... 510/102 |
| 6,635,775 B1 | | 10/2003 | Walele et al. |

FOREIGN PATENT DOCUMENTS

JP         2003137758    * 10/2001
WO        WO 9323364     *  5/1993

OTHER PUBLICATIONS

Technical Data Sheet, Solubility of Parsol 1789 in Finsolv TN, Finsolv TPP, Finsolv PG-22 and Finsolv EB, by Finetex, Inc., dated Nov. 1997.
Technical Data Sheet, Solubility of Benzophenone-3 in Finsolv TN, Finsolv TPP, Finsolv PG-22 and Finsolv EB, by Finetex, Inc., dated Nov. 1997.
Technical Data Sheet for FINSOLV® TPP, INCI Name: C12-15 Alkyl Benzoate (and) Dipropylene Glycol Dibenzoate (and) PPG-15 Stearyl Ether Benzoate, by Finetex, Inc., dated Apr. 2000.
Technical Data Sheet for FINSOLV® PG-22, INCI Name: Dipropylene Glycol Dibenzoate, by Finetex, Inc., dated Apr. 2000.
Technical Data Sheet for FINSOLV® EB, INCI Name: Ethylhexyl Benzoate, by Finetex, Inc., dated Jun. 21, 2002.
Finetex® Cosmetics & Personal Care Products Index, by Finetex, Inc., dated Mar. 2002.
Excerpt (pp. 1 and 5) from the website of Dermatest GmbH, http://www.dermatest.de/EN/Presentation/body_presentation.html, entitled "Presentation of Dermatest GmbH", download date Mar. 9, 2005.

* cited by examiner

*Primary Examiner*—Thurman K. Page
*Assistant Examiner*—Chukwuma Nwaonicha
(74) *Attorney, Agent, or Firm*—William J. Davis; Walter Katz

(57) ABSTRACT

An active or functional organic compound is solubilized in a phenylethyl ester, e.g. an aryl carboxylic ester of 2-phenylethyl alcohol, as a solvent, cosolvent or additive, to form a composition thereof. Representative active or functional organic compounds include personal care products, e.g. sunscreens containing UVA/UVB absorbing compounds, such as avobenzone and benzophenone-3. Such compositions also show increased critical wavelength and UVA/UVB absorbance ratio performance properties.

4 Claims, No Drawings

COMPOSITIONS CONTAINING PHENETHYL ARYL ESTERS AS SOLUBILIZING AGENTS FOR ACTIVE ORGANIC COMPOUNDS

BACKGROUND OF THE INVENTION

1. Field of the Invention

This invention relates to compositions containing an active or functional organic compound which requires solubilization, and more particularly, to such compositions which are effectively solubilized by addition of an aryl phenylethyl ester as solvent, cosolvent or additive.

2. Description of the Prior Art

Many commercial products, e.g. personal care, e.g. sunscreens, pharmaceutical, agricultural and industrial compositions, contain active or functional materials which require solubilization in the form of a solution, emulsion or dispersion, in aqueous or non-aqueous form. For example, a sunscreen formulation containing aromatic compounds such as avobenzone (Escalol® 517) and/or benzophenone-3 (Escalol® 567) as active UVA/UVB absorbing ingredients, requires a solubilization agent to keep it in an emulsion, i.e. to prevent crystallization. Several such solubilizers are known, e.g. ethyl benzoate or a $C_{12}$–$C_{15}$ alkyl benzoate; however, the former compound is a strong irritant, and the latter is only a poor solvent for avobenzone.

Previous syntheses of 2-phenylethyl benzoate have employed toxic solvents and/or expensive or toxic stoichiometric reagents. For example, 2-phenylethyl alcohol and benzoic acid have been condensed in acetonitrile solvent with the aid of a stoichiometric N,N,N',N'-tetramethylchloroformamidinium chloride reagent, prepared in situ from N,N,N',N'-tetramethylurea, oxalyl chloride and pyridine (Fujisawa et al., *Chem. Lett.* 1982, 1891–1894). (Oxalyl chloride is a toxic liquid and generates carbon monoxide, a toxic gas.) Similarly, they have been condensed in tetrahydrofuran solvent with the aid of a stoichiometric 3-methylbenzothiazole-2-selone/diethyl azodicarboxylate/N,N-dimethylaniline reagent (Mitsunobu et al., *Chem. Lett.* 1984, 855–858), and they have also have been condensed with the aid of a stoichiometric triphenylphosphine/S-benzyl-S-phenyl-N-p-tosylsulfilimine reagent (Aida et al., Chem. Lett. 1975, 29–32). (The selenium and phosphorous by-products create a toxic waste problem.) They have also been condensed in toluene with catalytic toluenesulfonic acid, prepared in situ from toluene and sulfuric acid (Zardecki et al., Polish Patent, PL 55230, issued May 15, 1968). 2-Phenylethyl benzoate has also been prepared from 2-phenylethyl alcohol and benzoic anhydride in dichloromethane solvent with vanadium salts as catalysts (Chen, U.S. Pat. No. 6,541,659, issued Apr. 1, 2003) or with bismuth tris(trifluoromethanesulfonate) catalyst (Orita et al., *Angew. Chem.* Int. Ed. 2000, vol. 39, 2877–2879). It has also been prepared from 2-phenylethyl alcohol and benzoic anhydride in N,N-dimethylformamide solvent with equimolar 1,1,3,3-tetramethylguanidine (Kim et al., *Bull. Korean Chem. Soc*. 1984, vol. 5, 205–206).

Accordingly, it is an object of this invention to provide a composition including an active or functional organic compound, which is solubilized by a safe and effective organic solvent such as an aryl carboxylic ester of 2-phenylethyl alcohol, e.g. 2-phenylethyl benzoate, 2-phenylethyl toluate or di-2-phenylethyl phthalate.

Another object is to provide a personal care, e.g. a sunscreen, cosmetic, pharmaceutical, agricultural or industrial composition containing a solid, active or functional organic compound which is solubilized.

A specific object of the invention is to provide a sunscreen composition containing active UVA and/or UVB compounds, which are solubilized by a phenylethyl ester, and show excellent performance properties including increased critical wavelength and UVA/UVB absorbance ratio.

A further object herein is to solubilize at least 20%, preferably 30% w/w or more of the active with the solubilizer of the invention.

A specific object of the invention is to provide a process for the synthesis of the solubilizer that economically affords a product with low color and low odor and that has a low environmental impact (no solvents, no stoichiometric reagents, no dangerous by-products, etc.; cf. 'green chemistry').

These and other objects and features of the invention will be made apparent from the following description.

SUMMARY OF THE INVENTION

What is described herein is a composition of an active or functional organic compound solubilized in a phenylethyl ester which is an aryl carboxylic ester of 2-phenylethyl alcohol.

In preferred forms of the invention, the phenylethyl ester is 2-phenylethyl benzoate, toluate or phthalate, the active or functional organic compound is a solid organic compound, e.g. a personal care, cosmetic, sunscreen, pharmaceutical, agricultural or industrial compound; most preferably an active sunscreen ingredient, e.g. a sunscreen composition containing UVA and/or UVB chemical compounds, e.g. avobenzone and/or benzophenone-3, and wherein the sunscreen composition exhibits an increased critical wavelength and UVA/UVB absorbance ratio.

Preferably the active is solubilized in an amount of at least 20%, most preferably 30% w/w or more with the solubilizer of the invention.

Another feature of the invention is the provision of a process for producing 2-phenylethyl benzoate, toluate or phthalate, which comprises heating a mixture 2-phenylethyl alcohol and the carboxylic acid with a tin catalyst and recovering the product.

DETAILED DESCRIPTION OF THE INVENTION

A. Precess for Mking Solublilizer

The process for making the invention solubilizer will be illustrated by the examples below. Accordingly, the 2-phenylethyl benzoate solubilizer was prepared by reacting 2-phenylethyl alcohol (2-phenylethanol) and benzoic acid in the presence of a catalyst, e.g. a Lewis acid catalyst such as tin oxalate (FASCAT 2001®, Atofina Chemicals), at temperatures above ca. 180° C., preferably at ca. 210° C., or a Brønsted ('strong') acid catalyst such as methanesulfonic acid, preferably at ca. 150° C. Additives such as triisodecylphosphite (TDP) and hypophosphorous acid (HPA) can improve the color of the product, but may decrease the reaction rate. Purification involves distillation of excess 2-phenylethyl alcohol or extraction of excess benzoic acid with aqueous sodium carbonate and treatment with activated carbon. The 2-phenylethyl o-toluate and 2-phenylethyl p-toluate analogs were made in a similar manner using o-methylbenzoic acid or p-methylbenzoic acid, respectively, in place of benzoic acid. Anhydrides are useful starting materials, as shown by the preparation of di-2-phenylethyl phthalate from phthalic anhydride and 2-phenylethyl alcohol, and esters can also be used, as illustrated by the preparation of 2-phenylethyl benzoate from methyl benzoate and 2-phenylethyl alcohol.

B. INVENTION COMPOSITIONS

Formulations such as sunscreen compositions containing active UVA and UVB compounds, e.g. avobenzone and benzophenone-3, were effectively solubilized in 2-phenylethyl benzoate, toluate or phthalate, and the UVA component of their absorption spectrum was enhanced relative to the UVB portion in this composition. Other actives such as cosmetic, pharmaceutical, agricultural and industrial compounds are effectively solubilized by 2-phenylethyl benzoate or related esters, including such actives as antibacterial and herbicidal, e.g. algaecidal, compounds, particularly to keep the active in emulsion form without crystallizing or precipitating out of the emulsion, and without requiring the use of large amounts of solvent.

C. Invention Examples

EXAMPLE 1

Preparation of 2-Phenylethyl Benzoate (0.1% Tin Catalyst)

A 2-L, 4-neck round bottom flask, fitted with a thermometer, mechanical stirrer, nitrogen inlet tube and Liebig condenser/receiving flask, was charged with 671.7 g (5.50 mol, 1.00 equiv) of benzoic acid, 806.3 g (6.60 mol, 1.20 equiv) of 2-phenylethyl alcohol, and 1.25 g (0.1% w/w) of Fascat 2001®. The system was heated gently with slow stirring (<50 rpm) until the benzoic acid dissolved. The air was removed with three cycles of evacuation/nitrogen fill using a mechanical vacuum pump (50–100 torr). The rate of stirring was increased to ca. 200 rpm, the nitrogen sparge was set at 0.2 scfh, and the reaction mixture was heated to 180° C. After a 1-h hold, the temperature was increased to 190° C. for 1 h and then to 200° C. for 1 h. The temperature was increased to 210° C. and the nitrogen sparge was increased to 0.5 scfh. After a 1-h hold, the temperature was further increased to 220° C. for 1 h. The total amount of distillate was 159.2 g, from which 94.4 g of water (theor. 99.1 g) was separated as the top layer. The reaction mixture was cooled to room temperature and sampled for analysis. The acid number was 1.10 mg KOH/g (99.7% conversion) and the APHA color was 115. The excess 2-phenylethyl alcohol (5.5% by GLC) was removed by vacuum distillation. Thus, after 1 h at 180–190° C. and 20 torr (0.5 scfh nitrogen sweep), the residual 2-phenylethyl alcohol was <0.05% by GLC and the APHA color was 222. Activated carbon (37.3 g, 3% w/w) was added, and the mixture was heated at 75–80° C. under vacuum (50–70 torr) for 1 h. After cooling to room temperature, filtration through Celite® gave 1100 g (90%) of 2-phenylethyl benzoate. The APHA color was 20, the acid number was 0.14 mg KOH/g, the saponification number was 246 mg KOH/g (theor. 248), and the residual tin was <10 ppm.

EXAMPLE 2

Preparation of 2-Phenylethyl Benzoate (0.2% Tin Catalyst)

The reaction set-up was similar to Example 1, except that 2.5 g (0.2% w/w) of Fascat 2001® was used. The reaction was significantly faster and was complete after 1-h holds at 180° C., 190° C., 200° C. and 210° C. After distillation of the excess 2-phenylethyl alcohol (5.4% by GLC) and treatment with activated carbon as above, the yield was 1150 g (92%) of 2-phenylethyl benzoate. The residual 2-phenylethyl alcohol was <0.05% by GLC, the APHA color was 20, the acid number was 0.58 mg KOH/g, the saponification number was 245 mg KOH/g, and the residual tin was 150 ppm.

EXAMPLE 3

Preparation of 2-Phenylethyl Benzoate (0.1% Tin Catalyst with TDP)

The reaction was run as described in Example 1, and after 5 h at 180–220° C., the acid number was 3.2 mg KOH/g, the APHA color was 44, and the excess 2-phenylethyl alcohol was 3.5% by GLC. A 1.25-g portion of triisodecylphosphite (TDP) was added, and the excess 2-phenylethyl alcohol was distilled as usual. The APHA color was 42. Treatment with activated carbon as usual gave 1140 g (92%) of 2-phenylethyl benzoate. The residual 2-phenylethyl alcohol was <0.05% by GLC, the APHA color was 13, the acid number was 0.30 mg KOH/g, the saponification number was 244 mg KOH/g, the residual tin was <10 ppm, and the residual phosphorous was <10 ppm.

EXAMPLE 4

Preparation of 2-Phenylethyl Benzoate (0.2% Tin Catalyst with TDP)

The reaction was run as described in Example 2, and after 4 h at 180–210° C., the reaction mixture was cooled to room temperature, where the acid number was 3.80 (98.4% conversion), the APHA color was 33, and the excess 2-phenylethyl alcohol was 4.7% by GLC. A 1.24-g (0.1% w/w) portion of triisodecylphosphite (TDP) was added, and the excess 2-phenylethyl alcohol was removed by vacuum distillation as usual, during which time a white solid formed. No change was apparent upon cooling to 25° C., where the residual 2-phenylethyl alcohol was <0.05% by GLC and the APHA color was 35. Treatment with activated carbon as usual afforded 1130 g (91%) of 2-phenylethyl benzoate. The APHA color was 14, the acid number was 0.57 mg KOH/g, the saponification number was 244 mg KOH/g, the residual tin was 60 ppm, and the residual phosphorous was <10 ppm.

When the same amount of TDP was charged along with the starting materials instead of immediately before vacuum distillation, the reaction was significantly slower; therefore, an additional 1-h hold at 220° C. was added. The APHA color was 26 and the excess 2-phenylethyl alcohol was 4.7% by GLC. After vacuum distillation as usual, the residual 2-phenylethyl alcohol was <0.05% by GLC and the APHA color was 36. Treatment with activated carbon as usual afforded 1090 g (88%) of 2-phenylethyl benzoate. The APHA color was 13, the acid number was 0.14 mg KOH/g, the saponification number was 243 mg KOH/g, the residual tin was <10 ppm, and the residual phosphorous was <10 ppm.

EXAMPLE 5

Preparation of 2-Phenylethyl Benzoate (0.2% Tin Catalyst with HPA)

The reaction was run as described in Example 2 except that the initial excess of 2-phenylethyl alcohol was 10% rather than 20%, and the organic layer that co-distilled with the water of reaction was returned to the batch at the end of each hold but the last one. After 4 h at 180和 210° C., the reaction mixture was cooled to room temperature, where the acid number was 5.50 (97.8% conversion), the APHA color was 114, and the excess 2-phenylethyl alcohol was 4.8% by GLC. A 9.94-g aliquot of 50% w/w aqueous hypophosphorous acid (H PA, 0.40% w/w based on $H_3PO_2$) was added. The excess 2-phenylethyl alcohol was removed by vacuum distillation as usual. The APHA color was 39 and the residual 2-phenylethyl alcohol was 0.19% by GLC. Treatment with activated carbon as usual afforded 1100 g (88%) of 2-phenylethyl benzoate. The APHA color was 36, the acid number was 2.10 mg KOH/g, the saponification number was 244 mg KOH/g, the residual tin was 270 ppm, and the residual phosphorous was 1300 ppm.

When half the amount of HPA (0.2% w/w based on $H_3PO_2$) was charged along with the starting materials instead of immediately before vacuum distillation, the reaction was significantly slower, and additional 1-h holds at 220° C., 230° C. and 240° C. were added. The acid number was 11.5 mg KOH/g (96.0% conversion). The excess 2-phenylethyl alcohol (4.1% by GLC) was removed by vacuum distillation as usual. The residual 2-phenylethyl alcohol was <0.05% by GLC, the APHA color was 45, and the acid number was 1.50 mg KOH/g. Treatment with activated carbon as usual afforded 1030 g (83%) of 2-phenylethyl benzoate. The APHA color was 27, the acid number was 1.24 mg KOH/g, the saponification number was 244 mg KOH/g, the residual tin was <10 ppm and the residual phosphorous was 335 ppm.

EXAMPLE 6

Preparation of 2-Phenylethyl Benzoate (Other Tin Catalysts)

The reaction was run as described in Example 1 except that 1.25 g of Fascat 4201® (dibutyltin oxide) was used instead of Fascat 2001® (tin oxalate), and after 7 h at 190–210° C., the acid number was 0.88 mg KOH/g (99.7% conversion), the APHA color was 102, and the excess 2-phenylethyl alcohol was 3.6% by GLC. After vacuum distillation as usual, the residual 2-phenylethyl alcohol was <0.05% by GLC and the APHA color was 177. Treatment with activated carbon as usual gave 1030 g (83%) of 2-phenylethyl benzoate. The APHA color was 89, the acid number was 0.22 mg KOH/g, the saponification number was 245 mg KOH/g, and the residual tin was 10 ppm.

The reaction was repeated as described in Example 1 except that 1.25 g of Fascat 4100® was used instead of Fascat2001®, and after 4 h at 190–210° C., the acid number was 5.70 mg KOH/g (97.7% conversion), the APHA color was 111, and the excess 2-phenylethyl alcohol was 4.8% by GLC. After vacuum distillation as usual, the residual 2-phenylethyl alcohol was 0.16% by GLC and the APHA color was 186. Treatment with activated carbon as usual gave 1010 g (81%) of 2-phenylethyl benzoate. The APHA color was 67, the acid number was 0.70 mg KOH/g, the saponification number was 244 mg KOH/g, and the residual tin was 10 ppm.

EXAMPLE 7

Preparation of 2-Phenylethyl Benzoate (Ester Exchange with Tin Catalyst)

The reaction was set up as in Example 2 except that methyl benzoate (748.8 g, 5.50 mol) was used instead of benzoic acid and 671.9 g (5.50 mol) of 2-phenylethyl alcohol was used. After 4 h at 190° C., 230 g of distillate was collected and the reaction mixture was 51% product by GLC. The methanol was stripped from the distillate on a Buchi rotary evaporator and the residue was returned to the reaction flask. The batch was heated for 2 h at 200° C. and 2 h at 210° C., whereupon 170 g of distillate was collected and the reaction mixture was 80% product by GLC. The methanol was stripped from the distillate as before, and the residue was returned to the reaction flask. The batch was heated for 2 h at 210° C. and 2 h at 220° C., whereupon 40 g of distillate was collected and the reaction mixture was 94% product by GLC. The excess 2-phenylethyl alcohol (3.5% by GLC) and methyl benzoate (2.7% by GLC) were removed by vacuum distillation as usual and the product was treated with activated carbon as usual to afford 1000 g (81%) of 2-phenylethyl benzoate. The residual 2-phenylethyl alcohol was 0.30, the APHA color was 40, the acid number was 0.13 mg KOH/g, the saponification number was 245 mg KOH/g, and the residual tin was <10 ppm.

EXAMPLE 8

Preparation of 2-Phenylethyl Benzoate (Strong Acid Catalyst)

A 2-L, 4-neck round bottom flask, fitted with a thermometer, mechanical stirrer, nitrogen inlet tube and Liebig condenser/receiving flask, was charged with 671.7 g (5.50 mol, 1.00 equiv) of benzoic acid, 806.3 g (6.60 mol, 1.20 equiv) of 2-phenylethyl alcohol, 5.30 g (0.43% w/w, 1.0 mol %) of methanesulfonic acid (MSA) and 1.25 g (0.1% w/w) of triisodecylphosphite (TDP). The system was heated gently with slow stirring (<50 rpm) until the benzoic acid dissolved. The air was removed with three cycles of evacuation/nitrogen fill using a mechanical vacuum pump (50–100 torr). The rate of stirring was increased to ca. 200 rpm, the nitrogen sparge was set at 0.2 scfh, and the reaction mixture was heated to 140° C. After a 1-h hold, the temperature was increased to 150° C. and held for 1 h. The temperature was increased to 160° C. and the nitrogen sparge was increased to 0.5 scfh. After a 1-h hold, the reaction mixture was cooled to room temperature and sampled for analysis. The acid number was 8.1 mg KOH/g (97.3% conversion of benzoic acid, corrected for MSA), the APHA color was 66, and the excess 2-phenylethyl alcohol was 7.9% by GLC. To the reaction mixture at 25° C. was added 213 g of 10% w/w aqueous sodium carbonate solution. The batch was heated to 50° C. and stirred for 15 min. The stirring was stopped and the batch was allowed to settle for 30 min. The bottom aqueous layer was removed from the flask with a pipette, and 2-phenylethyl alcohol was removed by vacuum distillation at 180–190° C. (20 torr) for 1 h with a nitrogen sweep of 0.5 scfh. The reaction mixture was cooled to ca. 70° C. and sampled for analysis. The residual 2-phenylethyl alcohol was 0.17% by GLC, the acid number was 0.10 mg KOH/g, and the APHA color was 95. Treatment with activated carbon and filtration as usual (see Example 1) gave 1100 g (88%) of 2-phenylethyl benzoate. The APHA color was 72, the acid number was 0.11 mg KOH/g, the saponification number was 242 mg KOH/g, the residual sulfur was <10 ppm, and the residual phosphorous was <10 ppm.

EXAMPLE 9

Preparation of 2-Phenylethyl Benzoate (Strong Acid Catalyst with HPA)

The reaction set up was the same as in Example 8, except that 10.6 g (2 mol %) of methanesulfonic acid (MSA) was used instead of 5.3 g (1 mol %), and 14.5 g of 50% w/w aqueous hypophosphorous acid (HPA, 0.58% w/w based on $H_3PO_2$) was added instead of TDP. After 1-h holds at 140° C., 150° C. and 160° C. as in the previous example, additional 1-h holds were added at 170° C. and 180° C. to complete the reaction. The acid number was 24.9 mg KOH/g (98.6% conversion of benzoic acid, corrected for MSA and HPA). The acid was removed by washing with 250 g of 15% w/w aqueous sodium carbonate solution at 50° C. and then with 250 g of water at 90° C. The batch was dried for 1 h at 75–80° C. (50–70 torr, 0.5 scfh nitrogen sweep) to give 1210 g (97%) of 2-phenylethyl benzoate. The residual 2-phenylethyl alcohol was 0.10% by GLC, the APHA color was 15, the acid number was 0.51 mg KOH/g, the saponification number was 243 mg KOH/g, the residual sulfur was 500 ppm, and the residual phosphorous was 200 ppm. The product had the odor of 'burned rubber,' which was removed by treatment with activated carbon as usual to give 1100 g (88%) of 2-phenylethyl benzoate. The residual 2-phenylethyl alcohol was 0.08% by GLC, the APHA color was 11, the acid number was 0.36 mg KOH/g, the saponification number was 244 mg KOH/g, the residual sulfur was 500 ppm, and the residual phosphorous was 200 ppm.

EXAMPLE 10

2-Phenylethyl Toluate

Both ortho and para-methylbenzoic acid were employed instead of benzoic acid in the procedure described in Example 2. The former yielded 1128 g (85%) of 2-phenylethyl ortho-toluate, and the latter yielded 1129 g (86%) of 2-phenylethyl para-toluate. The APHA color of the former (latter) was 203 (421), the acid number was <0.05 (0.15) mg KOH/g, the saponification number was 225 (228) mg KOH/g (theor. 233), and the residual tin was <10 (<10) ppm.

EXAMPLE 11

Di-2-phenylethyl Phthalate

A 2-L, 4-neck round bottom flask, fitted with a thermometer, mechanical stirrer, nitrogen inlet tube and Liebig condenser/receiving flask, was charged with 481.4 g (3.25 mol, 1.00 equiv) of phthalic anhydride, 814.0 g (6.66 mol, 2.05 equiv) of 2-phenylethyl alcohol, and 2.55 g (0.2% w/w) of Fascat 2001®. The air was removed with three cycles of evacuation/nitrogen fill using a mechanical vacuum pump (50–100 torr). The nitrogen sparge was set at 0.2 scfh, and the system was heated gently with slow stirring (<50 rpm) until the benzoic acid dissolved. A spontaneous reaction set in and no further heating was necessary until the reaction mixture reached ca. 100° C., whereupon GLC showed that the anhydride had reacted completely with the first equivalent of 2-phenylethyl alcohol. External heating was resumed until the reaction mixture reached 180° C., and the reaction was completed as described in Example 1. After the usual treatment with activated carbon, it was filtered through 200 g of activity I basic alumina and then 200 g of activity I silica gel to give 808 g (66%) of di-2-phenylethyl phthalate. The APHA color was 168, the acid number was 0.52 mg KOH/g, the saponification number was 301 mg KOH/g (theor. 300), and the residual tin was 195 ppm.

EXAMPLE 12

Solubility of Solid Organic Sunscreens in Various Solvents

Predetermined weight/weight (w/w) solutions were prepared at 50° C. using a given solvent and Escalol® 517 or Escalol® 567. The solutions were allowed to stand for 1 week at 25° C. in a constant temperature chamber. A small seed crystal was added at 25° C. to hasten equilibration. Solubility limits were determined by observation of the amount of solid present, and then more precisely by a GLC method (see Example 15).

TABLE 1

Solubility Data for Sunscreen Compounds

| Solvent | Escalol® 517% w/w | Escalol® 567% w/w |
|---|---|---|
| Controls | | |
| Ethyl benzoate | 33 | 44 |
| $C_{12-15}$ benzoate (Finsolv® TN) | 16 | 16 |
| Invention | | |
| 2-Phenylethyl benzoate | 24 | 35 |
| 2-Phenylethyl o-toluate | 24 | 33 |
| 2-Phenylethyl p-toluate | 26 | 33 |
| 2-Phenylethyl o & p-toluate (1:1) | 24 | 33 |
| Di-2-phenylethyl phthalate | 30 | 31 |

As shown above, the solubilizer of the invention is effective in solubilizing at least 20%, preferably 30% or more (w/w) of the active compound.

While the control ethyl benzoate is a very effective solvent, it is extremely harmful to the skin and eyes and therefore not acceptable for personal care use. The $C_{12-15}$ benzoate solvent is safe for personal care use, but is a much poorer solvent for these sunscreen compounds. The invention 2-phenylethyl esters, in contrast, are safe for personal care use and have excellent solubilizing power.

EXAMPLE 13

Enhancement of Escalol® 517 UVA Absorption

A 10-mg portion of Escalol® 517 was dissolved in 1 L of solvent, and the UV spectrum of the solution was measured using a Cary 1E UV-Visible Spectrophotometer.

TABLE 2

UVA Absorption Data

| Solvent | $\lambda_{max}$, nm |
|---|---|
| Ethanol | 358 |
| $C_{12-15}$ benzoate (Finsolv® TN) | 358 |
| 2-phenylethyl benzoate | 362 |

These results demonstrate that greater UVA protection is afforded for the active sunscreen using 2-phenylethyl benzoate instead of $C_{12-15}$ benzoate in the composition.

EXAMPLE 14

Anti-aging Cream Formulations

Typical Preparation: To prepare Phase A charge a beaker with water, butylene glycol and disodium EDTA. Begin mixing, and slowly sift in Stabileze® QM. Mix and heat to 80° C.; maintain this temperature and mix for 45 minutes. In a separate beaker combine the ingredients for Phase B. Mix and heat to 75° C. Slowly add Phase C to Phase A until the batch is clear, and then add Phase B to the mixture. Mix and cool the batch to 45° C. Add Phase D to the batch and mix well, then add Phase E and mix well. QS for water loss.

TABLE 3

Broad Spectrum UVA/UVB Sunscreen Formulations

| INGREDIENTS | 1 % w/w | 2 % w/w | 3 % w/w | 4 % w/w | 5 % w/w |
|---|---|---|---|---|---|
| Phase A | | | | | |
| Deionized water | 57.35 | 57.35 | 57.35 | 57.35 | 57.35 |
| Stabileze ® QM | 0.50 | 0.50 | 0.50 | 0.50 | 0.50 |
| Butylene glycol | 3.00 | 3.00 | 3.00 | 3.00 | 3.00 |
| Disodium EDTA | 0.10 | 0.10 | 0.10 | 0.10 | 0.10 |
| Phase B | | | | | |
| Cerasynt ® 840 | 1.50 | 1.50 | 1.50 | 1.50 | 1.50 |
| Cerasynt ® 945 | 2.00 | 2.00 | 2.00 | 2.00 | 2.00 |
| Escalol ® 557 | 7.50 | 7.50 | 7.50 | 7.50 | 7.50 |
| Escalol ® 517 | 3.00 | 3.00 | 3.00 | 3.00 | 3.00 |
| Escalol ® 587 | 5.00 | 5.00 | 5.00 | 5.00 | 5.00 |
| Escalol ® 567 | 2.00 | 2.00 | 2.00 | 2.00 | 2.00 |
| 2-Phenylethyl benzoate | 10.00 | 0.00 | 0.00 | 0.00 | 0.00 |
| Finsolv ® TN | 0.00 | 10.00 | 0.00 | 0.00 | 0.00 |
| Eldew ® SL-205 | 0.00 | 0.00 | 10.00 | 0.00 | 0.00 |
| Finsolv ® TPP | 0.00 | 0.00 | 0.00 | 10.00 | 0.00 |
| Elefac ® I-305 | 0.00 | 0.00 | 0.00 | 0.00 | 10.00 |
| Phase C | | | | | |
| Sodium hydroxide, 10% w/w | 1.30 | 1.30 | 1.30 | 1.30 | 1.30 |
| Deionized water | 5.00 | 5.00 | 5.00 | 5.00 | 5.00 |
| Phase D | | | | | |
| Liquapar ® Optima | 1.25 | 1.25 | 1.25 | 1.25 | 1.25 |
| Liquapar ® Oil | 0.40 | 0.40 | 0.40 | 0.40 | 0.40 |
| Phase E | | | | | |
| Glycacil ®-L | 0.100 | 0.100 | 0.100 | 0.100 | 0.100 |
| | 100.00 | 100.00 | 100.00 | 100.00 | 100.00 |

These formulations were examined for critical wavelength, a measure of UVA protection, using an Optometrics SPF 290 analyzer after five freeze-thaw cycles and then after 1 month of storage at 45° C. The higher the critical wavelength, the greater the UVA protection.

TABLE 4

Critical Wavelength Data

| Formulation | Freeze-thaw critical wavelength (nm) | Storage critical wavelength (nm) |
|---|---|---|
| 1 | 376.15 | 375.10 |
| 2 | 374.75 | 373.30 |
| 3 | 374.35 | 374.15 |
| 4 | 373.95 | 373.80 |
| 5 | 373.75 | 372.55 |

As can be seen for both the freeze-thaw and 1-month storage conditions, the formulation containing 2-phenylethyl benzoate was superior to formulations containing Finsolv® TN, Eldew® SL-205, Finsolv® TPP, and Elfac® I-305.

EXAMPLE 15

Solubility of Triclosan

5-Chloro-2-(2,4-dichlorophenoxy)phenol (Triclosan) has bacteriostatic properties and is used as a disinfectant and preservative in cosmetic and detergent preparations. It is soluble up to 69% w/w in 2-phenylethyl benzoate, as determined by GLC. Thus, 50% w/w and 60% w/w mixtures were homogeneous solutions at 25° C., but a 70% w/w solution prepared at 70° C. precipitated a small amount of solid when seeded at 25° C. and allowed to stand for 3 days.

An 80% w/w solution prepared from 8.002 g of Triclosan and 2.009 g of 2-phenylethyl benzoate precipitated a significant amount of solid at 25° C. A 23.3-mg sample of the supernatant was dissolved in 1.00 mL of chloroform and 1.00 µL was injected via automatic injector into a GLC instrument. The areas of the 2-phenylethyl benzoate and Triclosan peaks were 9381 and 12953, respectively. The mixture was heated at 70° C. until it was homogeneous, and an 18.2-mg sample was dissolved and injected in the same manner. The 2-phenylethyl benzoate peak had an area of 4456 units, which represented 3.6 µg, and the Triclosan peak had an area of 11240 units, which represented 14.6 µg. (Note that the amount injected was 3.6 µg+14.6 µg=18.2 µg.) Therefore, under our GLC conditions the response factors were 1240 units/µg and 770 units/µg, respectively. Then, the respective amounts of each component in the supernatant were 9381/1240 =7.6 µg and 12953/770 =16.8 µg, which corresponds to 69% w/w Triclosan.

EXAMPLE 16

Solubility of Nuocide® 1051 (ISP)

N-Cyclopropyl-N-(1,1-dimethylethyl)-6-(methylthio)-1,3,5-triazine-2,4-diamine (Nuocide® 1051) is an industrial algaecide used in formulating anti-fouling paints for boats. It is soluble up to 7% w/w in 2-phenylethyl benzoate and 28% w/w in 2-phenylethyl benzoate/N-methylpyrrolidinone (1:1 w/w).

EXAMPLE 17

Solubility of Prodiamine

5-Dipropylamino-α,α,α-trifluoro-4,6-dinitro-o-toluidine (Prodiamine) is a broad-spectrum pre-emergence agricultural herbicide. It is soluble up to 5% w/w in 2-phenylethyl benzoate and 24% w/w in 2-phenylethyl benzoate/N-methylpyrrolidinone (1:1 w/w).

While the invention has been described with particular reference to certain embodiments thereof, it will be understood that changes and modifications may be made which are within the skill of the art. Accordingly, it is intended to be bound only by the following claims.

What is claimed is:

1. A sunscreen composition of an active or functional organic sunscreen UVA and/or UVB absorbing compound selected from avobenzone and/or benzophenone-3 solubilized in a phenylethyl ester which is an aryl carboxylic ester of 2-phenylethyl alcohol wherein said active or functional sunscreen compound is solubilized in an amount of at least 20% w/w.

2. A sunscreen composition according to claim 1 wherein said phenylethyl ester is 2-phenylethyl benzoate, 2-phenylethyl toluate or di-2-phenylethyl phthalate.

3. A sunscreen composition according to claim 1 in which said active compound is a solid organic compound.

4. A sunscreen composition according to claim 1 wherein said phenylethyl ester is 2-phenylethyl benzoate.

* * * * *